US012590053B2

(12) United States Patent
Bestgen et al.

(10) Patent No.: US 12,590,053 B2
(45) Date of Patent: Mar. 31, 2026

(54) PROCESS FOR PREPARING VANILLIN (METH)ACRYLATES

(71) Applicant: Evonik Operations GmbH, Essen (DE)

(72) Inventors: Sebastian Bestgen, Eschborn (DE); Thorben Schütz, Alsbach-Haehnlein (DE); Tim Bleith, Mainz (DE); Günther Gräff, Bensheim (DE); Silvia Beyer, Ober-Ramstadt (DE); Tanja Nawrath, Bickenbach (DE)

(73) Assignee: Evonik Operations GmbH, Essen (DE)

( * ) Notice: Subject to any disclaimer, the term of this patent is extended or adjusted under 35 U.S.C. 154(b) by 511 days.

(21) Appl. No.: 18/044,516

(22) PCT Filed: Sep. 1, 2021

(86) PCT No.: PCT/EP2021/074069
§ 371 (c)(1),
(2) Date: Mar. 8, 2023

(87) PCT Pub. No.: WO2022/053357
PCT Pub. Date: Mar. 17, 2022

(65) Prior Publication Data

US 2023/0365487 A1 Nov. 16, 2023

(30) Foreign Application Priority Data

Sep. 10, 2020 (EP) .................................... 20195402

(51) Int. Cl.
*C07C 67/08* (2006.01)
*C07C 69/54* (2006.01)

(52) U.S. Cl.
CPC .............. *C07C 69/54* (2013.01); *C07C 67/08* (2013.01)

(58) Field of Classification Search
CPC ................................ C07C 67/08; C07C 69/54
See application file for complete search history.

(56) References Cited

U.S. PATENT DOCUMENTS 5,350,823 A 9/1994 Haeberle et al.
5,656,688 A 8/1997 Bauer et al.
(Continued)

FOREIGN PATENT DOCUMENTS

CN 105294957 * 2/2016 ............ A61K 47/32
DE 42 37 030 5/1994
(Continued)

OTHER PUBLICATIONS

Bukowska-Sluz, et al., Photoinitiated copolymerization of acetonyl mehacrylate, Journal of Thermal analysis and calorimetry, vol. 113, No. 2, pp. 909-913 (Year: 2012).*
(Continued)

*Primary Examiner* — Yate' K Cutliff
(74) *Attorney, Agent, or Firm* — Grüneberg Global IP, PLLC

(57) ABSTRACT

An improved process can be used for preparing vanillin (meth)acrylates and derivatives or structurally related compounds thereof in high purity, by reacting an alcohol with an activated (meth)acrylic acid derivative. Ethyl vanillin (meth) acrylate provides for improved room temperature crosslinking efficiency and is particularly suitable for paints/varnishes and coatings.

16 Claims, 1 Drawing Sheet

(56) References Cited

U.S. PATENT DOCUMENTS

| | | | | |
|---|---|---|---|---|
| 9,394,460 | B1 | 7/2016 | Yang et al. | |
| 2011/0144267 | A1 | 6/2011 | Schuetz et al. | |
| 2011/0196169 | A1* | 8/2011 | Knebel | C07C 67/08 560/140 |
| 2014/0228509 | A1 | 8/2014 | Yang et al. | |
| 2016/0297738 | A1* | 10/2016 | Klesse | C07C 67/62 |

FOREIGN PATENT DOCUMENTS

| | | |
|---|---|---|
| DE | 10 2013 223 876 | 5/2015 |
| EP | 0 016 518 | 10/1980 |
| EP | 2 246 403 | 11/2010 |
| WO | 94/25433 | 11/1994 |
| WO | 2009/146995 | 12/2009 |
| WO | 2010/026204 | 3/2010 |
| WO | 2017/007883 | 1/2017 |
| WO | 2018/063095 | 4/2018 |

OTHER PUBLICATIONS

Dikusar et al., Preparative synthesis of vanillin and vanillal esters of several carboxylic acids, Chemistry of Natural Compounds, Kluwer Academic publishers-consultants bureau, NE., vol. 41, No. 1, pp. 91-92 (Year: 2005).*

Eing et al., Visible light activation of spin-silenced fluorescence-Supporting Info., Chemistry a European Journal, vol. 24, No. 47, pp. 12246-12249, 16 supporting pages (Year: 2018).*

Stanzione III, et al., Vanillin-based resin for use in composite applications, Green Chemistry, 14, pp. 2346-2352 (Year: 2012).*

Bukowska-Śluz et al., “Photoinitiated copolymerization of acetonyl methacrylate”, J. Therm Anal Calorim, vol. 113, 2013, pp. 909-913.

Database Chemcats [Online] STN / 2-propenoic acid, 2-methyl, 2-ethoxy-4-formylphenyl ester, Registry No. 1134333-11-1; Entered STN: Apr. 14, 2009, 1 page.

Dikusar et al., “Preparative Synthesis of Vanillin and Vanillal Esters of Several Carboxylic Acids”, Chemistry of Natural Compounds, vol. 41, No. 1, 2005, pp. 91-92.

Eing et al., “Visible light-activation of spin-silenced fluorescence”, Chemistry: A European Journal, 2018, pp. S1-S15.

Fache et al., “Vanillin, a promising biobased building-block for monomer synthesis”, Green Chemistry, vol. 16, 2014, pp. 1987-1998.

International Search Report dated Nov. 26, 2021, in PCT/EP2021/074069, 6 pages.

Renbutsu et al., “Synthesis of UV-curable chitosan derivatives and palladium (II) adsorption behavior on their UV-exposed films”, Carbohydrate Polymers, vol. 69, 2007, pp. 697-706.

Stanzione III et al., “Lignin Model Compounds as Bio-Based Reactive Diluents for Liquid Molding Resins” ChemSusChem, vol. 5, 2012, pp. 1291-1297.

Written Opinion dated Nov. 26, 2021, in PCT/EP2021/074069, 6 pages.

* cited by examiner

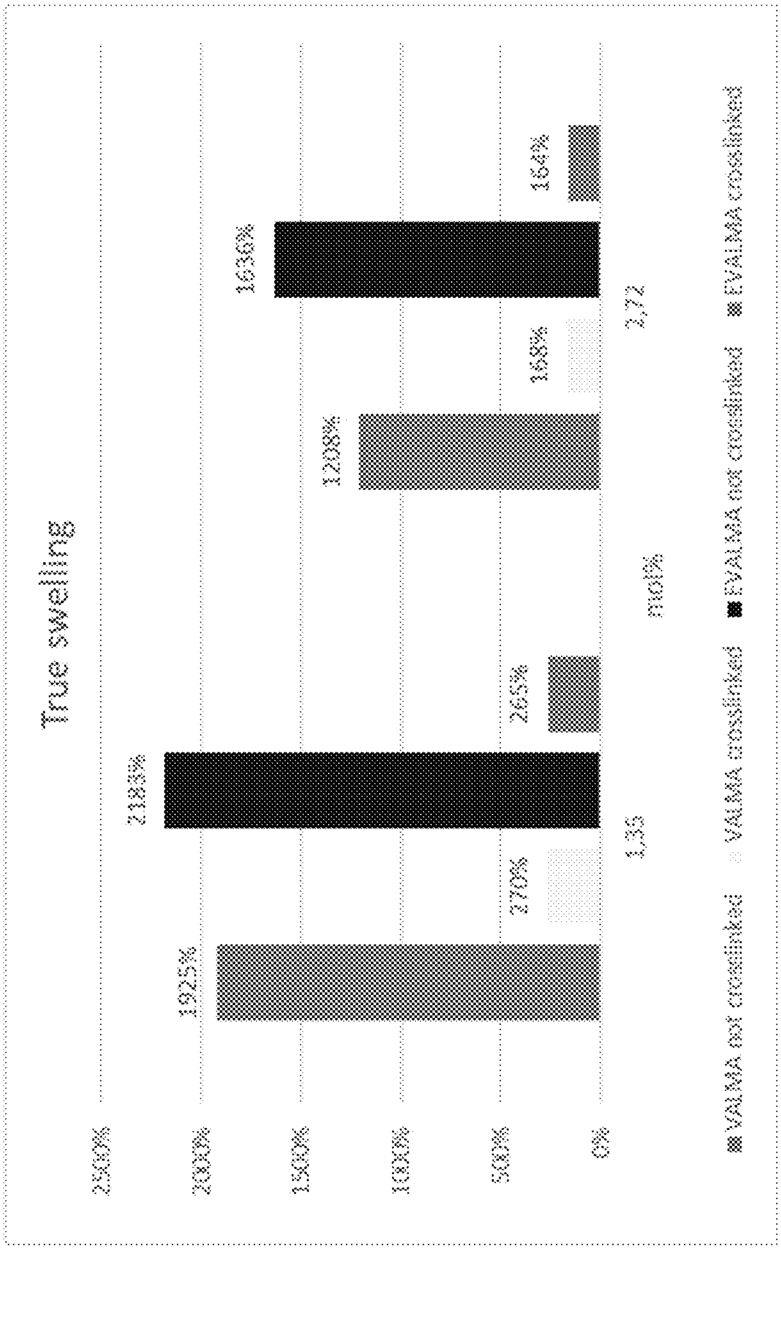
True swelling
2500%
2000%
1500%
1000%
500%
0%
1925%
270%
2183%
265%
1208%
168%
1636%
164%
1,35
2,72
mol%
VALMA not crosslinked
VALMA crosslinked
FVALMA not crosslinked
FVALMA crosslinked

PROCESS FOR PREPARING VANILLIN (METH)ACRYLATES

CROSS-REFERENCE TO RELATED APPLICATIONS

This application is the National Stage entry under § 371 of International Application No. PCT/EP2021/074069, filed on Sep. 1, 2021, and which claims the benefit of priority to European Application No. 20195402.1, filed on Sep. 10, 2020. The content of each of these applications is hereby incorporated by reference in its entirety.

BACKGROUND OF THE INVENTION

Field of the Invention

The invention pertains to a new process for preparing vanillin (meth)acrylates and derivatives or structurally related compounds thereof in high purity. The process is highly resource efficient and thus particularly suitable for large-scale syntheses. In addition, the present invention relates to ethyl vanillin (meth)acrylate, which may be advantageously applied in paints/varnishes and/or coatings.

Description of Related Art

Polymer latexes or dispersions are widely used in water-based coatings. The polymer latex or dispersion is dried to form a film via coalescence to obtain desired mechanical and physical properties. A method of improving the properties of films formed by water-borne compositions is to include polymers that are capable of crosslinking. The polymers may be self-crosslinking or dependent on the involvement of a crosslinking agent to react with the polymers.

Relatively recent coating materials comprise polymers containing carbonyl groups, such as vanillin (meth)acrylate, which can be cured by addition of crosslinking agents to give relatively solvent-resistant coatings.

Vanillin (meth)acrylate (VAL(M)A) is the (meth)acrylic acid ester of vanillin (4-Hydroxy-3-methoxybenzaldehyd), a nowadays important natural raw material resource. Vanillin is not only of value for its bioavailability, but also because it is a multifunctional molecule, whose carbonyl moiety allows for further reactivity and various post-functionalization steps. From a chemical point of view, vanillin (meth) acrylate can be described as a (meth)acrylic acid ester of a phenol derivative. Therefore, the synthesis of VAL(M)A requires the use of either (meth)acrylic acid chloride (or halide in general) or (meth)acrylic anhydride. Both routes have been described in the literature, with WO 2017/007883 A1 being a recent example.

VAL(M)A may be used for preparing organic polymers, as a monomer or co-monomer for polymer preparation, and as a reactive diluent for polymer preparation, e.g., thermoset polymers. Unsaturated polyester resins (UPR) and vinyl ester resins (VER) are widely used thermosetting polymers for fiber-reinforced composites. For example, global UPR market is approximately a 5,000 kilo ton business and is experiencing continued growth. Vinyl ester resins (VER) have been widely used as matrix materials for advanced polymer composites in various applications because of their excellent corrosion and degradation resistance, high glass transition temperature, high strength-to-weight ratios, and low cost. Until recently, petrochemicals were the resource of choice for production of commodity monomers for vinyl ester resins. However, the continued utilization of these non-renewable resources raises concerns regarding environmental pollution and depletion of non-renewable resources. Also, widely used petroleum-based monomers, such as styrene, are often used as reactive diluents with both vinyl ester resins and unsaturated polyesters. However, such reactive diluents are often considered hazardous air pollutants (HAPs) and volatile organic compounds (VOCs). Unsaturated polyester resins (UPR) and vinyl ester resins (VER) typically are mixed with styrene (in amounts up to 50%) as a reactive diluent before being cured by a free radical polymerization. However, styrene offers significant disadvantages owing to health, safety, and environmental concerns. Styrene is also derived from petroleum, a non-renewable resource. There exists a need for alternatives to styrene which overcome one or more of the shortcoming associated with the prior art.

In order to develop sustainable and environmentally friendly vinyl ester resins, the identification of renewable building blocks that substitute petroleum-based components in these resins has seen increasing efforts. Several renewable resources (cellulose, starch, natural oils, etc.) have been exploited to produce novel bio-monomers. However, most of these bio-monomers are aliphatic or cycloaliphatic, resulting in polymers with low structural rigidity and thermal stability (see e.g., M. Fache, et al., Green Chem 2014, 16, 1987).

Recently, attention has turned to bio-based phenolic compounds, such as lignin model compounds and cashew nutshell liquid-derived aromatics for high performance vinyl ester resins that exhibit similar or better properties than commercial petroleum-based products. Vanillin, originally an extraction product of vanilla plantifolia beans, is one of the most widely used flavors in foods, fragrances, beverages, and pharmaceuticals (see, e.g., C. Brazinha, et al., Green Chem 2011, 13, 2197). Certain vanillin derivatives have been used as renewable building blocks for high performance polymers mainly because of their rigid aromatic structures. The use of vanillin as a bio-resource for the production of novel polymeric materials is possible because it can be mass-produced from lignin, which is one of the most abundant feedstocks in nature, as wood contains approximately 30% lignin.

Vanillin has already been modified into methacrylated derivatives for vinyl ester resins, for example via Steglich esterification of vanillin with methacrylic acid as coating materials (E. Renbutsu, et al., Carbohyd Polym 2007, 69, 697), via esterification of vanillin with methacryloyl chloride (R. J. Patel, et al., Der Pharma Chemica 2013, 5, 63), or via reacting vanillin with methacrylic anhydride (Stanzione et al, Chemsuschem 2012, 5, 1291).

While the synthesis from (meth)acrylic anhydride and vanillin in the presence of a catalyst is known, subsequent workup of the crude reaction mixture has technically not been solved satisfactorily: The methods described in the art include the use of inert conditions, liquid-liquid extraction processes with (expensive, toxic, environmentally unfriendly) organic solvents, chromatographic purification processes as well as drying processes using desiccants.

However, a non-toxic, environmentally friendly and, at the same time, cost-efficient work-up is crucial for large-scale processes for producing VAL(M)A or its derivatives.

In view of the above, there was an urgent need for an improved process for preparing VAL(M) A (and its derivatives and structurally related compounds), which enables a resource-efficient preparation in large scale and in high purity.

SUMMARY OF THE INVENTION

Further, it is an objective of the present invention to provide monomers that are suitable for improving the properties of the above-mentioned coating materials. More particularly, those monomers ought to be able to be processed to dispersions and to polymers, emulsion polymers for example, which have a very low residual monomer content. The obtained polymer should be crosslinkable using the commonly applied crosslinking reagents, i.e. diamines and/or dihydrazides (such as ADH) and/or blocked crosslinking reagents such as blocked hydrazides as described in e.g. US 2014/0228509.

The above objectives were solved by the processes and compounds/compositions according to the present invention.

More specifically, the present invention provides a process for preparing (meth)acrylates of the general formula (I)

(I)

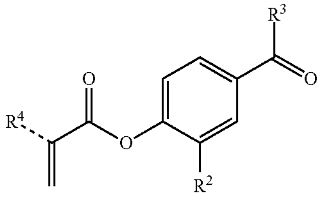

with $R^2$=—H, —OMe, —OEt, or —O—$C_3$ to O—$C_{10}$ alkyl, branched alkyl or alkenyl $R^3$=H, Me, Et, or —$C_3$ to $C_{10}$ alkyl or alkenyl $R^4$=—Me or —H by reacting an alcohol of the general formula (II)

(II)

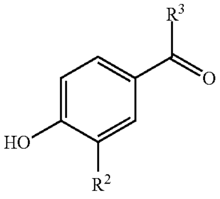

with $R^2$ being as defined above, and $R^3$=—H, —Me, —Et, or —$C_3$ to $C_{10}$ alkyl or alkenyl with an activated (meth)acrylic acid derivate (III)

(III)

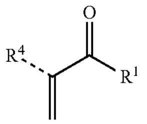

with $R^4$ being as defined above, and $R^1$=F, Cl, Br, I, —O(CO)C($CH_2$)$CH_3$, —O(CO)C($CH_2$)H wherein the (meth)acrylate of the general formula (I) is obtained from the crude reaction mixture by precipitation from an aqueous medium.

Further, the inventors have unexpectedly found that if the process is carried out in the presence of at least one polymerization inhibitor, said polymerization inhibitor co-precipitates with the (meth)acrylate of formula (I) and no further (additional) stabilization is required prior to storage or shipment. The present invention thus provides a stabilized (meth)acrylate of formula (I), obtainable by the aforementioned process, carried out in the presence of at least one polymerization inhibitor.

In addition to the above, the inventors have found that, surprisingly, the crosslinking properties of polymers including (meth)acrylate-based monomers of formulae (IV) or (V)

(IV)

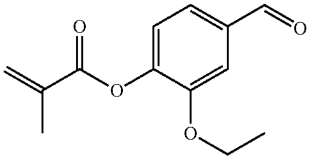

(V)

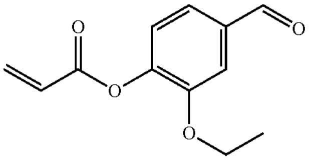

with commonly applied crosslinking reagents (i.e. diamines and/or a dihydrazides (such as ADH) and/or blocked crosslinking reagents such as blocked hydrazides) can be significantly improved versus their methoxy-analogues (i.e. vanillin (meth)acrylates).

Accordingly, the present invention also pertains to the (meth)acrylate of formula (IV) or of formula (V)

(IV)

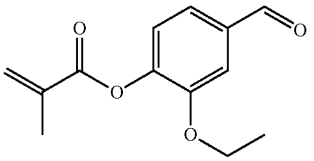

(V)

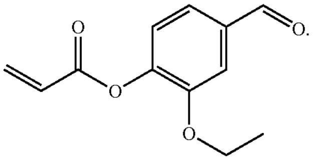

In the context of the present invention, the (meth)acrylate of formulae (IV) and (V) will be referenced as ethyl vanillin (meth)acrylate or as EVAL(M) A.

BRIEF DESCRIPTION OF THE DRAWING

The FIGURE is a diagram showing swelling behavior of crosslinked films.

DETAILED DESCRIPTION OF THE INVENTION

The inventors have unexpectedly found that highly pure VAL(M)A derived products can be prepared in a simple and resource-efficient manner via an esterification reaction of an alcohol of the general formula (II) with an activated (meth)

acrylic acid derivate (III), in which the isolation of the VAL(M)A derived product is conducted by simple precipitation from an aqueous medium. The method is particularly suitable for large-scale production, i.e. multi-kg to multi-ton scales.

Contacting the crude reaction mixture with an aqueous medium does not result in biphasic mixtures or sticky oils/oil drops. To the contrary, a purification effect occurs in the precipitation step, since the VAL(M)A derived product crystallizes in aqueous medium surprisingly quickly and no accumulation (co-precipitation) of impurities or other undesired compounds occurs in the VAL(M) A derived product. Particularly surprising, the aforementioned high product purity is obtained independent of the purity or quality of the starting materials, and in particular independent of the purity of (meth)acrylic acid anhydride (i.e. the content of (meth) acrylic acetic anhydride within the (meth)acrylic acid anhydride starting material).

In the context of the present invention, the terms "VAL (M)A derivative" and "VAL(M)A derived product" are used interchangeably and refer to vanillin (meth)acrylate, its derivatives and also to structurally similar or structurally related compounds of the general formula (I):

(I)

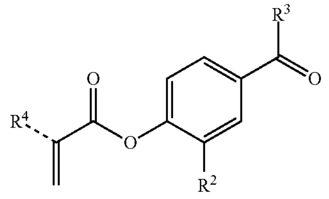

In preferred embodiments of the present invention, $R^3$ is hydrogen or methyl. $R^3$ being hydrogen is particularly preferred.

The term "(meth)acrylate" is understood to mean esters both of methacrylic acid and of acrylic acid.

The inventors have found that during the precipitation step according to the process of the present invention, (a) the product crystallizes and thus automatically separates from the reaction mixture;

(b) catalysts (that may optionally be present in the reaction mixture) and derivatives arising from the initially used catalyst are separated from the product, as they remain in the aqueous phase;

(c) excess or unreacted activated (meth)acrylic acid derivate (III) is quenched;

(d) by-products arising from the quenching process (e.g. (meth)acrylic acid, hydrogen chloride/halide) remain in the aqueous phase;

(e) no valuable—and potentially toxic or hazardous-organic solvents have to be used; and (e) inhibitors (that may optionally be present in the reaction mixture) used during the reaction co-precipitate and therefore remain in the VAL(M)A derived product.

Preferably, the (meth)acrylate of formula (I) is vanillin (meth)acrylate (VAL(M) A) or ethyl vanillin (meth)acrylate (EVAL(M) A).

The aqueous medium used in the precipitation step of the process according to the present invention may be selected from pure or desalted water, aqueous alcoholic solutions, aqueous ammonia solutions, aqueous (earth)alkali metal hydroxide solutions and aqueous (earth)alkali metal hydrogen carbonate and carbonate solutions. Aqueous alcoholic solutions are preferably solutions of methanol/ethanol in water (1 wt. % to 70 wt. %, preferably 30 wt. % to 70 wt. %).

Hydrogen carbonate solutions and carbonate solutions are advantageously saturated. The concentration of the ammonia solutions may be between 0.1 mol/l and 16.5 mol/l. The concentration of (earth)alkali metal hydroxide solutions may be between 0.01 mol/l and 1.0 mol/l.

Advantageously, the precipitation step is carried out at a pH between 7 and 12, preferably at a pH between 7-9.

The amount of aqueous medium used in the precipitation step is ideally between 1 to 20 times, preferably between 5 to 10 times the mass of alcohol (II) initially used. In order to initiate precipitation, the crude reaction mixture can be poured into the aqueous medium, or, alternatively the aqueous medium can be added to the crude reaction mixture.

The activated (meth)acrylic acid derivate (III) used in the present invention is preferably (meth)acrylic acid anhydride. The activated (meth)acrylic acid derivate (III) used in the reaction may be present in an amount of between 0.9 eq. and 2.0 eq, preferably between 1.0 eq. and 1.8 eq. and most preferably between 1.2 eq. and 1.6 eq., based on the amount of the alcohol of the general formula (II).

The reaction of the alcohol of the general formula (II) with the activated (meth)acrylic acid derivate (III) may be carried out under solvent-free conditions, preferably in the presence of at least one catalyst and/or at least one stabilizer (polymerization inhibitor).

The catalyst may advantageously be selected from the group consisting of alkaline metal salts (such as hydroxides, halides, triflates, perchlorates), alkaline earth metal salts (such as hydroxides, halides, triflates, perchlorates), zinc salts (such as hydroxides, halides, triflates, perchlorates), rare earth metal salts (such as halides, triflates, perchlorates), lithium alkoxides, sulfuric acid, lithium or sodium methacrylate, amino-substituted pyridines such as 4-(dimethylamino)-pyridine, or mixtures thereof. The aforementioned metal salts may be used in anhydrous or in hydrated form. Preferred amounts of catalyst are 0.1 to 10 mol %, particularly 5 mol % (relative to alcohol) for lithium alkoxide, sodium hydroxide or magnesium chloride; 0.1 to 2 wt %, particularly 0.5 wt % for sodium methacrylate; 0.1 to 1 wt % sulfuric acid (relative to total reaction mass), particularly 0.3 to 0.4 wt %. Preferred lithium alkoxide catalysts are LiOMe, LiOEt, LiOPr, LiOiPr, LiOBu and LiOiBu. Sulfuric acid may be used in concentrated or diluted from. Preferably, it is applied in amounts of between 0.01 wt % and 1.0 wt %, relative to the reaction mass. Ion exchange resins, such as amberlyst, can also be used for catalysis.

Preferred catalysts for the process according to the present invention are lithium methoxide, or magnesium chloride, or sodium hydroxide, or sodium (meth)acrylate or sulfuric acid, or mixtures thereof.

To prevent undesirable polymerization of the (meth) acrylates, polymerization inhibitors (stabilizers) can be used in the processes according to the present invention. Within the context of the present invention, the terms "(polymerization) inhibitor" and "stabilizer" are used synonymously.

Advantageously, these processes are performed in the presence of an inhibitor composition comprising or consisting of at least one phenolic polymerization inhibitor.

Advantageously, the process of the present invention is carried out in the presence of at least one polymerization inhibitor selected from the group consisting of hydroquinones, hydroquinone ethers such as hydroquinone monomethyl ether or di-tert-butylcatechol, phenothiazine, N,N'-(diphenyl)-p-phenylenediamine, 4-hydroxy-2,2,6,6-tetramethylpiperidin-1-oxyl, p-phenylenediamine, methylene blue or sterically hindered phenols, with an amount of stabilizer at the beginning of the reaction adjusted to between 0 and 5000 ppm, preferably between 1000 ppm and 3000 ppm based on the amount of theoretically expected product at full conversion.

Preferably, the polymerization inhibitor is selected from hydroquinone monomethyl ether, 2,4-Dimethyl-6-tert-butylphenol, 2,6-di-tert-butyl-4-methyl-phenol, Octadecyl-3-(3,5-di-tert-butyl-4-hydroxyphenyl)-propionate (such as IRGANOX 1076) and 4-hydroxy-2,2,6,6-tetramethylpiperidin-1-oxyl, and mixtures thereof. These inhibitors co-precipitate with the product (meth)acrylates of the general formula (I), meaning that spontaneous polymerizations in the final product can be avoided. The reaction of the alcohol of the general formula (II) with the activated (meth)acrylic acid derivate (III) is carried out at a temperature between 0° C. and 130° C., preferably at a temperature between 80° C. and 100° C. and most preferably between 85° C. and 95° C. Usually, reaction takes 3 h to 5 h up to full conversion, but may also be between 1 hour and 24 hours.

Preferably, the activated (meth)acrylic acid derivative (III) is used as its commercially available stabilized species (e.g. VISIOMER® MAAH), stabilized with an inhibitor outlined above.

Preferably, the activated (meth)acrylic acid derivative (III) is used as its commercially available stabilized species (e.g. VISIOMER® MAAH) with either 2000 ppm+-200 ppm 2,4-Dimethyl-6-tert-butylphenol or 1000 ppm+-200 ppm 2,4-Dimethyl-6-tert-butylphenol, thus already introducing one stabilizer into the reaction mixture and—as outlined—also in the final product.

Additional inhibitor may be added, preferably with an amount of additionally added stabilizer at the beginning of the reaction adjusted to between 0 and 1000 ppm based on the amount of theoretically expected product at full conversion, and most preferably with an amount of additionally added stabilizer at the beginning of the reaction adjusted to between 150 and 1000 ppm based on the amount of theoretically expected product at full conversion, The crude reaction mixture may be contacted with methanol prior to precipitating the (meth)acrylate of the general formula (I) from aqueous medium. In case this intermediate step is conducted, the methanol is preferably added at a temperature between 60° C. and 80° C. The amount of methanol added can be calculated and is 1 to 5 equivalents relative to residual (meth)acrylic anhydride present in the reaction mixture at the end of reaction.

In one embodiment of the present invention, alcohol of the general formula (II) is vanillin and the (meth)acrylates of the general formula (I) is vanillin (meth)acrylate. In a different embodiment, the alcohol of the general formula (II) is ethyl vanillin and the (meth)acrylates of the general formula (I) is ethyl vanillin (meth)acrylate.

In an additional aspect, the present invention provides a stabilized (meth)acrylate of formula (I), i.e. a composition comprising a (meth)acrylate of the general formula (I)

(I)

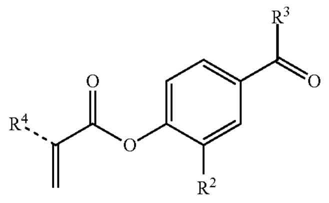

with $R^2$=—H, —OMe, —OEt, or —O—$C_3$ to O—$C_{10}$ alkyl, branched alkyl or alkenyl $R^3$=H, Me, Et, or —$C_3$ to $C_{10}$ alkyl or alkenyl $R^4$=—Me or —H and at least one polymerization inhibitor, the composition being obtainable by reacting an alcohol of the general formula (II)

(II)

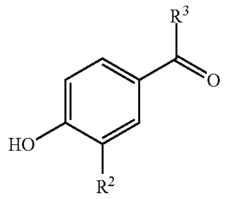

with $R^2$ and $R^3$ being as defined above, and with an activated (meth)acrylic acid derivate (III)

(III)

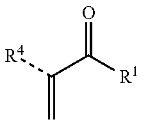

with $R^1$=F, Cl, Br, I, —O(C═O)C($CH_3$)($CH_2$), —O(C═O)C(H)($CH_2$), and with $R^4$ being as defined above, the reaction being carried out in the presence of said at least one polymerization inhibitor, and precipitating the (meth)acrylate of the general Formula (I) together with the at least one inhibitor from the crude reaction mixture by precipitation from an aqueous medium.

Suitable (meth)acrylates of formula (I) are as defined above. In preferred embodiments of the present invention, $R^3$ is hydrogen or methyl. $R^3$ being hydrogen is particularly preferred. Vanillin (meth)acrylate and ethyl vanillin (meth-acrylate), as well as 4-Acetylphenyl (meth)acrylate (formula (VI) and (VII), resp.) and 4-Formylphenyl (meth)acrylate (formula (VIII) and (VIX), resp.) are particularly preferred.

(VI)

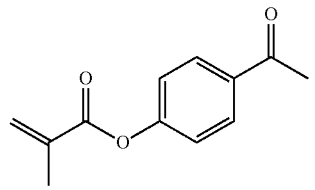

(VII)

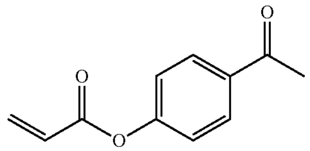

(VIII)

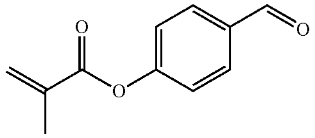

(VIX)

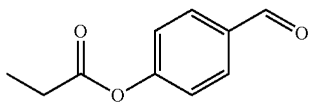

Suitable inhibitors are as defined above. Advantageously, 2,4-Dimethyl-6-tert-butylphenol (Topanol A), p-Methoxyphenol (MEHQ), 4-hydroxy-2,2,6,6-tetramethylpiperidin-1-oxyl and/or combinations thereof are used.

The inhibitors used in the process are preferably applied in amounts of between 0 and 5000 ppm, preferably between 1000 and 3000 ppm in total.

The thus-obtained stabilized (meth)acrylate of formula (I), (i.e. the composition comprising a (meth)acrylate of the general formula (I) at least one stabilizer has a stabilizer content of between 400 ppm and 2000 ppm. In general, the concentration of stabilizer in the product accounts for 30% to 80% of the initial stabilizer concentration in the reaction.

The inventors have unexpectedly found that the crosslinking properties of polymers including EVAL(M)A monomers of formulae (IV) or (V) with commonly applied crosslinking reagents (i.e. diamines and/or dihydrazides (such as ADH) and/or blocked crosslinking reagents such as blocked hydrazides) can be significantly improved versus vanillin (meth)acrylates. As shown on comparative experiments, room-temperature crosslinking is more efficient for polymers incorporating EVAL(M) A instead of VAL(M)A as experiments on EVAL(M)A based polymers/films indicate an increased crosslinking density.

Accordingly, the invention is also directed to the (meth) acrylate of formula (IV) or of formula (V)

(IV)

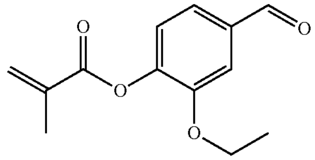

-continued (V)

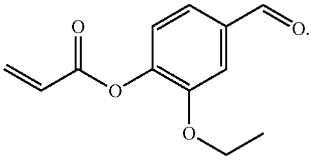 [SMILES: C=CC(=O)Oc1ccc(C=O)cc1OCC]

The compounds of formulae (IV) and (V) are obtainable via the processes according to the present invention. As may be obvious in view of the above, the invention also refers to stabilized (meth)acrylates of formula (IV) or of formula (V), obtainable by the processes as described in the above.

The compounds and compositions according to the present invention or obtainable by the processes of the present invention, respectively, are particularly suitable as co-monomer and reactive diluent for (emulsion) polymer preparation (UPR, VER), as described e.g. in WO 94/025433, WO 2010/026204, DE 10 2013 223 876, EP 0016518, DE 4237030, WO 2009/146995A1, EP 2246403, U.S. Pat. No. 9,394,460B1 and WO2018063095A1.

Further, the compounds and compositions according to the present invention or obtainable by the processes of the present invention, respectively, are particularly suitable as co-monomers in crosslinking poly(meth)acrylate binders having functionalized monomers such as, acetone monomers, diacetoneacrylamide (DAAM), acetoacetoxyethyl (meth)acrylate (AAE(M)A) monomers, butyl acetoacetate (BAA) monomers or mixtures thereof. Thereby, the compounds described in this invention are suitable co-monomers for (partial) replacement of or addition to common carbonyl-containing compounds (such as DAAM), used in current and commonly established formulations.

Polymer emulsions (sometimes called "latexes") are commonly used film formers in the coatings and paints industry. These aqueous-dispersible polymer compositions typically comprise an organic polymer binder phase dispersed in an aqueous solvent phase. These polymer emulsions may be curable/crosslinkable at room temperature conditions (typically around 20° C.-30° C.). The polymer binder phase of such emulsions is typically comprised of polymers or copolymers having actinic-radiation curable functional groups, such as vinyl groups. A common example of such binders would be polyacrylates or polymethacrylates. A crosslinking agent is usually added to such compositions to increase the hardness of an ultimately formed coating. This is accomplished by increasing the crosslinking density. Apart from enhanced hardness, other benefits of increasing crosslinking density may include, but are not limited to, increased coating resistance to water or chemical solvents (acids, bases), cleanability, and (wet) scrub-resistance.

Crosslinking can be performed using commonly applied crosslinking reagents, i.e. diamines and/or dihydrazides (such as ADH) and/or blocked crosslinking reagents such as blocked hydrazides as described in e.g. US 2014/0228509.

In the following, the invention is illustrated by non-limiting examples and exemplifying embodiments

EXAMPLES

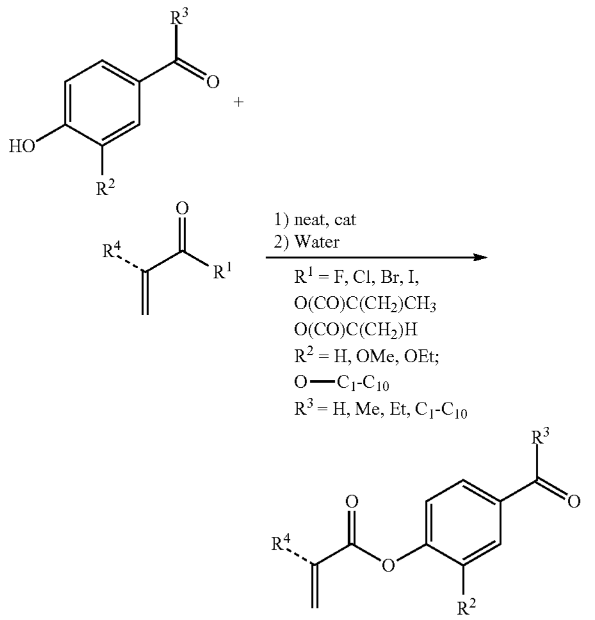

Example 1a: Synthesis of Vanillin Methacrylate (VALMA)($R^1$=$O(CO)C(CH_2)CH_3$, $R^2$=OMe, $R^3$=H, $R^4$=Me)

Vanillin (989 g, 6.5 mol, 1.00 eq.) and methacrylic acid anhydride (1402 g, 9.1 mol, 1.40 eq.) are mixed together with 4-Methoxyphenol (1.43 g, 0.011 mol, 0.001 eq.) and lithium methoxide (12.34 g, 0.32 mol, 5 mol %). The resulting mixture is heated to 90° C.-100° C., upon which a homogeneous solution is obtained. During the reaction, air is constantly bubbled through the reaction mixture. After four hours, methanol (346 g) is added and the mixture is additionally stirred at elevated temperature for 30 minutes. Subsequently, water (5 L) is added, which leads to precipitation of a colorless, crystalline solid. The solid is filtered off, optionally washed with water and dried. Yield: 1200 g (84%)

The as-obtained product already contains co-precipitated inhibitor 4-methoxyphenol as well as 2,4-Dimethyl-6-tert-butylphenol (arising from methacrylic anhydride) in sufficient amounts and does not have to be stabilized with polymerization inhibitors additionally.

$^1$H NMR (400.13 MHZ, $CDCl_3$): δ[ppm]=2.08 (dd, $^4J$=1.5 Hz, $^4J$=0.9 Hz, 3H, $CH_3$), 3.89 (s, 3H, $OCH_3$), 5.79 (dq, $^2J$=1.5 Hz, $^4J$=1.5 Hz, 1H, $CCH_2$), 6.38 (dq, $^2J$=1.5 Hz, $^4J$=0.9 Hz, 1H, $CCH_2$), 7.24-7.27 (m, 1H, CH), 7.46-7.52 (m, 2H, CH), 9.95 (s, 1H, COH).

$^{13}$C {1H} NMR complies with literature.

Reference: Stanzione, J. F., III, Sadler, J. M., La Scala, J. J. and Wool, R. P. (2012), Lignin Model Compounds as Bio-Based Reactive Diluents for Liquid Molding Resins. ChemSusChem, 5:1291-1297. doi: 10.1002/cssc.201100687

GC (Area-%): >97% purity (vanillin methacrylate). Residual Methacrylic anhydride <0.1, residual methacrylic acid <0.2

Inhibitor content: 1360 ppm 2,4-Dimethyl-6-tert-butylphenol, 488 ppm 4-methoxyphenol

Example 1b: Synthesis of Vanillin Methacrylate (VALMA)($R^1$=$O(CO)C(CH_2)CH_3$, $R^2$=OMe, $R^3$=H, $R^4$=Me)

Vanillin (800 g, 5.26 mol, 1.00 eq.) and methacrylic acid anhydride (1135 g, 7.37 mol, 1.40 eq.) are mixed together with 4-Methoxyphenol (1.16 g, 0.009 mol, 0.001 eq.) and sodium methacrylate (4 g, 0.037 mol, 0.007 eq.). The resulting mixture is heated to 90° C., upon which a homogeneous solution is obtained. During the reaction, air is constantly bubbled through the reaction mixture. After six hours, the mixture is poured into water (2 L), which leads to precipitation of a colorless, crystalline solid upon stirring. The solid is filtered off, optionally washed with water and dried. Yield: 850 g (74%)

The as-obtained product already contains co-precipitated inhibitor 4-methoxyphenol as well as 2,4-Dimethyl-6-tert-butylphenol (arising from methacrylic anhydride) in sufficient amounts and does not have to be stabilized with polymerization inhibitors additionally.

The analytical data compare well with the purity of VALMA obtained in example 1a.

Inhibitor content: 742 ppm 2,4-Dimethyl-6-tert-butylphenol, 253 ppm 4-methoxyphenol

Example 1c: Synthesis of Vanillin Methacrylate (VALMA)($R^1$=$O(CO)C(CH_2)CH_3$, $R^2$=OMe, $R^3$=H, $R^4$=Me)

Vanillin (4944.9 g, 32.5 mol, 1.00 eq.) and methacrylic acid anhydride (7014.3 g, 45.5 mol, 1.40 eq.) are mixed together with 4-Methoxyphenol (7.16 g, 0.057 mol, 0.001 eq.) and lithium methoxide (61.72 g, 1.62 mol, 5 mol %). The resulting mixture is heated to 90° C., upon which a homogeneous solution is obtained. During the reaction, air is constantly bubbled through the reaction mixture. The reaction is monitored via GC and consumption of starting material is almost complete after one hour (reaction could be stopped at this point). After 4.5 hours, methanol (2082.6 g) is added and the mixture is additionally stirred at elevated temperature for two hours. Subsequently, the reaction mixture is brought to room temperature. The crude material is poured into water, which leads to precipitation of a colorless, crystalline solid upon intense stirring. The product is separated from the mother liquor by filtration, additionally washed with water and dried. Yield: 6149 g (86%).

Nota bene: Additional product can be obtained from delayed precipitation in or extraction of the mother liquor. Extraction can be conducted with common organic solvents.

The as-obtained product already contains co-precipitated inhibitor 4-methoxyphenol as well as 2,4-Dimethyl-6-tert-butylphenol (arising from methacrylic anhydride) in sufficient amounts and does not have to be stabilized with polymerization inhibitors additionally.

GC (Area-%): >98% purity (vanillin methacrylate). Residual Methacrylic anhydride <0.2, residual methacrylic acid <0.1

Water content (Karl Fischer): <0.1 wt %

Inhibitor content: 848 ppm 2,4-Dimethyl-6-tert-butylphenol 205 ppm 4-methoxyphenol

Example 2: Synthesis of Ethylvanillin Methacrylate (EVALMA)($R^1$=$O(CO)C(CH_2)CH_3$, $R^2$=OEt, $R^3$=H, $R^4$=Me)

Ethylvanillin (200 g, 1.20 mol, 1.00 eq.) and methacrylic acid anhydride (259 g, 1.68 mol, 1.40 eq.) are mixed together with 4-Methoxyphenol (0.281 g, 0.002 mol, 0.001 eq.) and lithium methoxide (2.30 g, 0.06 mol, 5 mol %). The resulting mixture is heated to 90° C.-100° C., upon which a homogeneous solution is obtained. During the reaction, air is constantly bubbled through the reaction mixture. After 3.5 hours, methanol (47.7 g) is added and the mixture is additionally stirred at elevated temperature for 30 minutes. Subsequently, water (2 L) is added, which leads to precipitation of a colourless, crystalline solid. The solid is filtered off, optionally washed with water and dried. Yield: 268.8 g (95%)

The as-obtained product already contains co-precipitated inhibitor 4-methoxyphenol as well as 2,4-Dimethyl-6-tert-butylphenol (arising from methacrylic anhydride) in sufficient amounts and does not have to be stabilized with polymerization inhibitors additionally.

$^1$H NMR (400.13 MHZ, $CDCl_3$): δ [ppm]=1.38 (t, $^3J$=7.4 Hz, 3H, $CH_2CH_3$), 2.07 (dd, $^4J$=1.5 Hz, $^4J$=0.9 Hz, 3H, $CH_3$), 4.12 (q, $^3J$=7.4 Hz, 2H, $OCH_2$), 5.77 (dq, $^2J$=1.5 Hz, $^4J$=1.5 Hz, 1H, $CCH_2$), 6.38 (dq, $^2J$=1.5 Hz, $^4J$=0.9 Hz, 1H, $CCH_2$), 7.24-7.27 (m, 1H, CH), 7.45-7.49 (m, 2H, CH), 9.93 (s, 1H, COH).

$^{13}$C {$^1$H} NMR (100.61 MHZ, $CDCl_3$): δ [ppm]=14.5 ($CH_3$), 18.4 ($CH_3$), 64.7 ($OCH_2$), 112.0 (CH), 123.4 (CH), 124.5 (CH), 127.6 ($CH_2$), 135.1 ($C_q$), 135.4 ($C_q$), 145.6 ($C_q$), 151.4 ($C_q$), 164.9 (COO), 191.1 (COH).

GC (Area-%): >97% purity (Ethylvanillin methacrylate). Residual Methacrylic anhydride <0.1, residual methacrylic acid <0.2

Inhibitor content (double determination): 693 ppm and 727 ppm 2,4-Dimethyl-6-tert-butylphenol; 6 ppm and 20 ppm 4-methoxyphenol

Example 3: Synthesis of 4-Acetylphenylmethacrylate ($R^1$=O(CO)C($CH_2$)$CH_3$, $R^2$=H, $R^3$=Me, $R^4$=Me)

4-Hydroxyacetophenon (300 g, 2.20 mol, 1.00 eq.) and methacrylic acid anhydride (475.6 g, 3.09 mol, 1.40 eq.) are mixed together with 2,4-Dimethyl-6-tert-butylphenol (0.45 g, 0.002 mol, 0.001 eq.) and magnesium chloride (5.20 g, 2.5 mol %). The resulting mixture is heated to 90° C.-100° C., upon which a homogeneous solution is obtained. During the reaction, air is constantly bubbled through the reaction mixture. After 3 hours, methanol (35.2 g) is added and the mixture is additionally stirred at elevated temperature for 30 minutes. Subsequently, the mixture is poured into water (4 L), which leads to precipitation of a colorless, crystalline solid. The solid is filtered off, optionally washed with water and dried. Yield: 328.1 g (74%)

The as-obtained product already contains co-precipitated 2,4-Dimethyl-6-tert-in sufficient amounts and does not have to be stabilized with polymerization inhibitors additionally.

$^1$H NMR (400.13 MHZ, $CDCl_3$): δ [ppm]=2.08 (dd, $^4J$=1.5 Hz, $^4J$=0.9 Hz, 3H, $CH_3$), 2.59 (s, 3H, $CH_3$), 5.93 (dq, $^2J$=1.5 Hz, $^4J$=1.5 Hz, 1H, $CCH_2$), 6.31 (dq, $^2J$=1.5 Hz, $^4J$=0.9 Hz, 1H, $CCH_2$), 7.30-7.45 (m, 2H, CH), 8.00-8.07 (m, 2H, CH).

$^{13}$C{$^1$H} NMR (100.61 MHZ, $CDCl_3$): δ [ppm]=18.4 ($CH_3$), 17.2 ($CH_3$), 123.5 (CH), 128.7 ($CH_2$), 130.3 (CH), 135.0 ($C_q$), 135.5 ($C_q$), 154.7 ($C_q$), 165.4 (COO), 197.3 (COMe).

GC (Area-%): >98% purity (vanillin methacrylate). Residual Methacrylic anhydride <0.1, residual methacrylic acid <0.1.

Inhibitor content: 404 ppm 2,4-Dimethyl-6-tert-butylphenol

Example 4: Synthesis of 4-Formylphenylmethacrylate ($R^1$=O(CO)C($CH_2$)$CH_3$, $R^2$=H, $R^3$=H, $R^4$=Me)

4-Hydroxybenzaldehyd (200 g, 1.63 mol, 1.00 eq.) and methacrylic acid anhydride (353.5 g, 2.29 mol, 1.40 eq.) are mixed together with 2,4-Dimethyl-6-tert-butylphenol (0.31 g, 0.002 mol, 0.001 eq.) and lithium methoxide (3.10 g, 5 mol %). The resulting mixture is heated to 90° C.-100° C., upon which a homogeneous solution is obtained. During the reaction, air is constantly bubbled through the reaction mixture. After 4.5 hours, methanol (86.5 g) is added and the mixture is additionally stirred at elevated temperature for 30 minutes. Subsequently, the mixture is poured into aqueous ethanol (2 L, 70:30), which leads to precipitation of a colorless, crystalline solid upon cooling. The solid is filtered off, optionally washed with water and dried. The product is a liquid at room temperature.

GC (Area-%): >95% purity. Residual Methacrylic anhydride <0.1, residual methacrylic acid <0.2. The as-obtained product already contains co-precipitated inhibitor 2,4-Dimethyl-6-tert-butylphenol in sufficient amounts and does not have to be stabilized with polymerization inhibitors additionally.

$^1$H NMR (400.13 MHZ, $CDCl_3$): δ [ppm]=2.06 (dd, $^4J$=1.4 Hz, $^4J$=0.9 Hz, 3H, $CH_3$), 5.80 (dq, $^2J$=1.4 Hz, $^4J$=1.5 Hz, 1H, $CCH_2$), 6.37 (dq, $^2J$=1.4 Hz, $^4J$=0.9 Hz, 1H, $CCH_2$), 7.29-7.35 (m, 2H, CH), 7.90-7.95 (m, 2H, CH), 9.98 (s, 1H, CHO).

$^{13}$C{$^1$H} NMR (100.61 MHZ, $CDCl_3$): δ [ppm]=18.1 ($CH_3$), 122.3 (CH), 127.9 ($CH_2$), 131.0 (CH), 133.8 ($C_q$), 135.3 ($C_q$), 155.6 ($C_q$), 164.9 (COO), 190.7 (COH).

$^1$H NMR and $^{13}$C{$^1$H} NMR comply with literature.

Reference: M. Eing, B. T. Tuten, J. P. Blinco, C. Barner-Kowollik, Chem. Eur. J. 2018, 24, 12246.

Inhibitor content after recrystallization: 80 ppm 2,4-Dimethyl-6-tert-butylphenol Inhibitor-Content:

Synthetic procedures starting from methacrylic anhydride come along with inherent inhibitor content arising from the raw material. The methacrylic anhydride used in the above experiments typically contains 2,4-Dimethyl-6-tert-butylphenol (2000+−200 ppm) already. Hence, additional inhibitor does not have to be added during the synthesis necessarily, although e.g. 4-methoxyphenol may be added in addition. Naturally, the inhibitor content of the final product strongly depends on the yield, purity and exact workup procedure (washing, amount of water, basic or acidic conditions, recrystallisation etc.) and in the case of a solid product, also inhomogeneous inhibitor distribution within the solid must be considered. However, surprisingly, for all products and various work-up conditions, a sufficient amount of inhibitor remains in the product.

When a crude reaction mixture arising from the reaction of an alcohol with an activated methacrylic acid species is poured in or mixed with pure water, most of 2,4-Dimethyl-6-tert-butylphenol remains in the final product. Keeping in mind the weight increase of the product, the inhibitor concentration (in ppm) naturally lowers, when no extra inhibitor is added. For the above mentioned examples, the following is calculated and measured:

| Example 1a | | | | |
|---|---|---|---|---|
| | Methacrylic anhydride (g used) | Vanillin (g used) | VALMA (100 yield, theory) | VALMA (84% yield, practice) |
| Mass [g] | 1402.00 | 989.00 | 1431.00 | 269.00 |
| 2,4-Dimethyl-6-tert-butylphenol [g] | 2.80 | 0.00 | 2.80 | |
| 2,4-Dimethyl-6-tert-butylphenol [ppm] | 2000.00 | 0.00 | 1959.47 | 1360.00 |

| Example 1b | | | | |
|---|---|---|---|---|
| | Methacrylic anhydride (g used) | Vanillin (g used) | VALMA (100 yield, theory) | VALMA (74% yield, practice) |
| Mass [g] | 1135.00 | 800.00 | 1157.00 | 269.00 |
| 2,4-Dimethyl-6-tert-butylphenol [g] | 2.27 | 0.00 | 2.27 | |
| 2,4-Dimethyl-6-tert-butylphenol [ppm] | 2000.00 | 0.00 | 1961.97 | 742.00 |

| Example 1c | | | | |
|---|---|---|---|---|
| | Methacrylic anhydride (g used) | Vanillin (g used) | VALMA (100 yield, theory) | VALMA (86% yield, practice) |
| Mass [g] | 7014.00 | 4944.00 | 7157.00 | 6149.00 |
| 2,4-Dimethyl-6-tert-butylphenol [g] | 14.03 | 0.00 | 14.03 | |
| 2,4-Dimethyl-6-tert-butylphenol [ppm] | 2000.00 | 0.00 | 1960.04 | 848.00 |

| Example 2 | | | | |
|---|---|---|---|---|
| | Methacrylic anhydride (g used) | Ethylvanillin (g used) | EVALMA (100 yield, theory) | EVALMA (95% yield, practice) |
| Mass [g] | 259.00 | 200.00 | 281.00 | 269.00 |
| 2,4-Dimethyl-6-tert-butylphenol [g] | 0.52 | 0.00 | 0.52 | |
| 2,4-Dimethyl-6-tert-butylphenol [ppm] | 2000.00 | 0.00 | 1843.42 | 710.00 |

| Example 3 | | | | |
|---|---|---|---|---|
| | Methacrylic anhydride (g used) | 4-Hydroxy-acetophenon (g used) | 4-Acetylphenyl-methacrylate (100 yield, theory) | 4-Acetylphenyl-methacrylate (74% yield, practice) |
| Mass [g] | 475.60 | 300.00 | 450.00 | 328.00 |
| 2,4-Dimethyl-6-tert-butylphenol [g] | 0.95 | 0.00 | 0.95 | |
| 2,4-Dimethyl-6-tert-butylphenol [ppm] | 2000.00 | 0.00 | 2113.78 | 404.00 |

| Example 4 | | | | |
|---|---|---|---|---|
| | Methacrylic anhydride (g used) | 4-Hydroxy-benzaldehyd (g used) | 4-Formylphenyl-methacrylate (100 yield, theory) | 4-Formylphenyl-methacrylate (recrystallized) |
| Mass [g] | 475.60 | 300.00 | 450.00 | 328.00 |
| 2,4-Dimethyl-6-tert-butylphenol [g] | 0.95 | 0.00 | 0.95 | |
| 2,4-Dimethyl-6-tert-butylphenol [ppm] | 2000.00 | 0.00 | 2113.78 | 80.00 |

Indeed, 2,4-Dimethyl-6-tert-butylphenol is largely preserved during the reaction and remains in the product to a significant extend in case of a simple aqueous workup. Whereas almost no residual inhibitor is found in the aqueous washing phase, some amount gets lost in combination with the organic byproducts, such as methacrylic acid and methyl methacrylate). In contrast, upon recrystallization of products in organic solvents (see e.g. example 4), inhibitor gets lost.

That is, surprisingly:

a) When an activated and stabilized (meth)acrylic acid derivative is reacted with an alcohol as described above, no additional inhibitor must be added necessarily b) When the crude reaction mixture is simply worked up by mixing with an aqueous medium, the inhibitor arising from the stabilized (meth)acrylic acid derivative is largely preserved and remains in the product c) Literature-known workup procedures such as recrystallizations, chromatographic purification steps etc lower the final inhibitor concentration in the product and necessitate separate addition of inhibitor.

d) For VALMA and EVALMA: Related to the inhibitor concentration [in ppm] of the activated and stabilized (meth)acrylic acid component used, the inhibitor concentration of the product accounts for 30%-80% of the initial concentration.

Manufacturing of Dispersions, Subsequent Crosslinking Thereof with Adipic Acid Dihydrazide (ADH) and Manufacturing of Films.

Example 1: Synthesis of a Dispersion with Ethylvanillin Methacrylate (1.35 mol %)Butyl Acrylate Co Methyl Methacrylic, Ethylvanillin Methacrylate, Methacrylic Acid BuA-co-MMA-EVALMA-MAS=53.49-42.77-2.74-1 (wt. %)

Ethylvanillinmethacrylate (21.9 g) was dissolved in butyl acrylate (BuA, 427.9 g) and methyl methacrylate (342.2 g). The solution was emulsified (using a Ultra-Turrax, 3 minutes, 4000 rpm) with methacrylic acid (8 g), ammonium persulfate (APS, 2.4 g), Disponol FES 32 (0.6 g, 30%) in water (718.4 g). To a 2 L glass reactor, equipped with temperature control and blade stirrer, water (470 g) and Disponil DES 32 (0.6 g, 30%) were added, heated to 80° C. and mixed with APS (0.6 g) dissolved in water (10 g). After five minutes, the initially prepared emulsion was added over the course of 240 minutes (which may happen in intervals). After complete addition of the emulsion, the mixture was stirred additionally for one hour at 80° C. After cooling to room temperature, the dispersion was filtered using a filter with mesh size 125 μm. The as prepared dispersion had a content of solids of 40±1 wt %, a pH value of 2.1, a viscosity of 9 mPas, a rDNC-value of 100 nm and a minimum film formation temperature of 3.4° C. Prior to further reprocessing, the dispersion was adjusted to pH=9 via addition of aqueous ammonia (25%).

Example 2: Synthesis of a dispersion with ethylvanillin methacrylate (2.72 mol %)

Butyl acrylate co methyl methacrylic, ethylvanillin methacrylate, methacrylic acid BuA-co-MMA-EVALMA-MAS=52-41.56-5.45-1 (wt. %)

The dispersion was synthesized according to the procedure denoted in example 1, but using 43.6 g ethylvanillin methacrylate, 416.0 g butyl acetate, 332.5 methyl methacrylate and 8 g methacrylic acid. The as prepared dispersion had a content of solids of 40±1 wt %, a pH value of 2.0, a viscosity of 9 mPas, a rDNC-value of 112 nm and a minimum film formation temperature of 5.3° C. Prior to further reprocessing, the dispersion was adjusted to pH=9 via addition of aqueous ammonia (25%).

Example 3: Synthesis of a Dispersion with Vanillin Methacrylate (1.35 mol %)Butyl Acrylate Co Methyl Methacrylic, Vanillin Methacrylate, Methacrylic Acid BuA-co-MMA-VALMA-MAS=53.58-42.87-2.59-1 (wt. %)

The dispersion was synthesized according to the procedure denoted in example 1, but using 20.72 g vanillin methacrylate, 428.64 g butyl acetate, 342.72 methyl methacrylate and 8 g methacrylic acid. The as prepared dispersion had a content of solids of 40±1 wt %, a pH value of 2.0, a viscosity of 8 mPas, a rDNC-value of 111 nm and a minimum film formation temperature of 4.4° C. Prior to further reprocessing, the dispersion was adjusted to pH=9 via addition of aqueous ammonia (25%).

Example 4: Synthesis of a Dispersion with Vanillin Methacrylate (2.72 mol %)Butyl Acrylate Co Methyl Methacrylic, Vanillin Methacrylate, Methacrylic Acid BuA-co-MMA-VALMA-MAS=52.17-41.7-5.14-1 (wt. %)

The dispersion was synthesized according to the procedure denoted in example 1, but using 41.1 g vanillin methacrylate, 417.4 g butyl acetate, 333.6 methyl methacrylate and 8 g methacrylic acid. The as prepared dispersion had a content of solids of 40±1 wt %, a pH value of 1.9, a viscosity of 8 mPas, a rDNC-value of 122 nm and a minimum film formation temperature of 6.9° C. Prior to further reprocessing, the dispersion was adjusted to pH=9 via addition of aqueous ammonia (25%).

Crosslinking of Dispersions with Adipic Acid Dihydrazide (ADH)

All dispersions were crosslinked with equimolar amounts of ADH. An aqueous solution of ADH (15%) was added to a stirred dispersion and subsequently stirred for two hours. At room temperature, a film was dried up.

Solvent Uptake

The solvent uptake of prepared films was determined using methyl isobutyl ketone (MIBK). A sample (A) of a dispersion film was macerated/swelled up with MIBK for four hours at room temperature. Subsequently, the sample was taken out of the solvent, cleaned from excess adherent solvent and weighed. After that, die sample was dried for one hour at 140° C. and weighed again (B). The difference in weight of (A) and (B) accounts for the weight loss, which corresponds to the solvent uptake.

The swelling was related to the weight of sample (B) after removal of all soluble parts and is termed true swelling.

| Composition | | | | | |
|---|---|---|---|---|---|
| | | VALMA | | EVALMA | |
| mol % | Functional Monomer | 1.35 | 2.72 | 1.35 | 2.72 |
| | Butyl acrylate | 48.09 | 47.42 | 48.09 | 47.42 |
| | Methyl methacrylate | 49.23 | 48.52 | 49.23 | 48.52 |
| | Methacrylic acid | 1.33 | 1.34 | 1.33 | 1.34 |
| Weight-% | Functional Monomer | 2.59 | 5.14 | 2.74 | 5.45 |
| | Butyl acrylate | 53.58 | 52.17 | 53.49 | 52 |
| | Methyl methacrylate | 42.84 | 41.7 | 42.77 | 41.56 |
| | Methacrylic acid | 1 | 1 | 1 | 0.99 |

| Analytics | | | | |
|---|---|---|---|---|
| Content of solids | 39.14% | 39.30% | 39.45% | 39.33% |
| pH | 2.0 | 1.9 | 2.1 | 2.0 |
| Viscosity | 8 mPa * s | 8 mPa * s | 9 mPa * s | 9 mPa * s |
| $r_{DNC}$ | 111 nm | 122 nm | 100 nm | 112 nm |
| Min. film formation temp. | 4.4° C. | 6.9° C. | 3.4° C. | 5.3° C. |

Dispersions and Films

| alkaline, not crosslinked | | | | | |
|---|---|---|---|---|---|
| Appearance | Disperison Film | light beige tan, clear | light beige tan, clear | light beige tan, clear | light beige tan, clear |
| MIBK | True swelling | 1925% | 1208% | 2183% | 1636% |

| alkaline, crosslinked with ADH | | | | | |
|---|---|---|---|---|---|
| Appearance | Dispersion Film | light beige tan, clear | light beige brown, clear | light beige tan, clear | light beige tan, clear |
| | True swelling | 270% | 168% | 265% | 164% |

The swelling behavior of the crosslinked films is depicted in the FIGURE

As clearly seen in the swelling experiments of VALMA and EVALMA films, the absolute gap of true swelling values for non-crosslinked and crosslinked films differs significantly depending on the applied monomer. For EVALMA, the true swelling value of as-prepared films decreases to a greater extend (1.35 mol %: Δ (not-crosslinked: crosslinked)=−1918%, 2.72 mol %: Δ (not-crosslinked: crosslinked)=−1472%) as compared to VALMA-based films (1.35 mol %: Δ (not-crosslinked: crosslinked)=−1655%, 2.72 mol %: Δ (not-crosslinked: crosslinked)=−1040%)

Crosslinked films which incorporate polymers based on EVALMA show consistently lower true swelling values compared with films which incorporate polymers based on VALMA. For both applied molar concentrations of 1.35 mol % and 2.72 mol %, EVALMA shows lower true swelling values (265% and 164%) of crosslinked films than VALMA (270% and 168%).

Therefore, it is evident that the crosslinking of polymers with e.g. ADH is more efficient, when ethyl vanillin methacrylate is used instead of vanillin methacrylate. The same applies for ethyl vanillin acrylate vs. vanillin acrylate.

The invention claimed is:

1. A process for preparing a (meth)acrylate of the general formula (I)

(I)

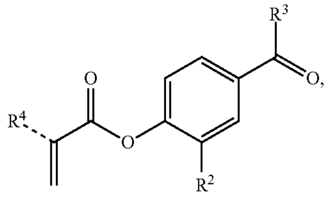

wherein $R^2$=—H, —OMe, —OEt, or —O—$C_3$ to O—$C_{10}$ alkyl, branched alkyl, or alkenyl, $R^3$=H, Me, Et, or —$C_3$ to $C_{10}$ alkyl or alkenyl, $R^4$=—Me or —H, the process comprising:

reacting an alcohol of the general formula (II)

(II)

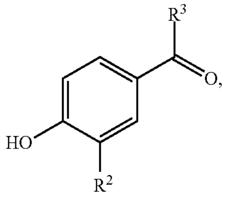

wherein $R^2$ and $R^3$ are as defined above, with an activated (meth)acrylic acid derivate (III)

(III)

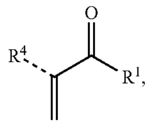

wherein $R^4$ is as defined above, and $R^1$=—O(CO)C($CH_2$)$CH_3$, or —O(CO)C($CH_2$)H, and precipitating the (meth)acrylate of the general formula (I) from a crude reaction mixture with an aqueous medium, wherein the reaction of the alcohol of the general formula (II) with the activated (meth)acrylic acid derivate (III) is carried out under solvent-free conditions, and the aqueous medium in the precipitation is selected from the group consisting of pure water, desalted water, an aqueous alcoholic solution, an aqueous ammonia solution, an aqueous (earth)alkali metal hydroxide solution, an aqueous (earth)alkali metal hydrogen carbonate solution, and a carbonate solution.

2. The process according to claim 1, wherein the precipitation is carried out at a pH between 7 and 12, and/or wherein an amount of the aqueous medium in the precipitation is between 1 to 20 times of a mass of the alcohol of the general formula (II).

3. The process according to claim 1, wherein the activated (meth)acrylic acid derivate (III) is methacrylic acid anhydride.

4. The process according to claim 1, wherein the alcohol of the general formula (II) is vanillin and the (meth)acrylate of the general formula (I) is vanillin (meth)acrylate, or alternatively, wherein the alcohol of the general formula (II) is ethyl vanillin and the (meth)acrylate of the general formula (I) is ethyl vanillin (meth)acrylate.

5. The process according to claim 1, wherein the reaction of the alcohol of the general formula (II) with the activated (meth)acrylic acid derivate (III) is carried out in the presence of at least one catalyst selected from the group consisting of an alkaline metal salt, an alkaline earth metal salt, a zinc salt, a rare earth metal salt, a lithium alkoxide, sulfuric acid, lithium methacrylate, sodium methacrylate, an amino-substituted pyridine, and a mixture thereof.

6. The process according to claim 1, wherein the reaction of the alcohol of the general formula (II) with the activated (meth)acrylic acid derivate (III) is carried out in the presence of lithium methoxide, magnesium chloride, sodium hydroxide, sodium (meth)acrylate, sulfuric acid, or a mixture thereof.

7. The process according to claim 5, wherein
- the at least one catalyst is lithium alkoxide, sodium hydroxide, or magnesium chloride, and is present in an amount of between 0.1 and 10 mol %, relative to the alcohol of the general formula (II);
- the at least one catalyst is sodium methacrylate, and is present between 0.1 and 2 wt %, relative to a total reaction mass; or
- the at least one catalyst is sulfuric acid, and is present between 0.1 and 1 wt %, relative to the total reaction mass.

8. The process according to claim 1, wherein the activated (meth)acrylic acid derivate (III) is present in an amount of between 0.9 eq. and 2.0 eq, based on an amount of the alcohol of the general formula (II).

9. The process according to claim 1, wherein the reaction of the alcohol of the general formula (II) with the activated (meth)acrylic acid derivate (III) is carried out at a temperature between 0° C. and 130° C.

10. The process according to claim 1, wherein the crude reaction mixture is contacted with methanol prior to precipitating the (meth)acrylate of the general formula (I) with the aqueous medium.

11. The process according to claim 1, wherein the reaction of the alcohol of the general formula (II) with the activated (meth)acrylic acid derivate (III) is carried out in the presence of at least one polymerization inhibitor selected from the group consisting of a hydroquinone, a hydroquinone ether, di-tert-butylcatechol, phenothiazine, N,N'-(diphenyl)-p-phenylenediamine, 4-hydroxy-2,2,6,6-tetramethylpiperidin-1-oxyl, p-phenylenediamine, methylene blue, and a sterically hindered phenol,
- wherein an amount of the polymerization inhibitor at the beginning of the reaction is adjusted to between 0 and 5000 ppm, based on an amount of theoretically expected product at full conversion.

12. A (meth)acrylate of formula (V)

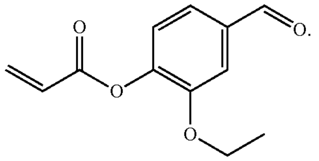

13. The process according to claim 5, wherein the at least one catalyst selected from the group consisting of an alkaline metal hydroxide, an alkaline metal halide, an alkaline metal triflate, an alkaline metal perchlorate, an alkaline earth metal hydroxide, an alkaline earth metal halide, an alkaline earth metal triflate, an alkaline earth metal perchlorate, a zinc hydroxide, a zinc halide, a zinc triflate, a zinc perchlorate, a rare earth metal halide, a rare earth metal triflate, a rare earth metal perchlorate, 4-(dimethylamino)-pyridine, and a mixture thereof.

14. The process according to claim 7, wherein
- the at least one catalyst is the lithium alkoxide, the sodium hydroxide, or the magnesium chloride, and is present in an amount of 5 mol %, relative to the alcohol of the general formula (II);
- the at least one catalyst is the sodium methacrylate, and is present in an amount of 0.5 wt %, relative to the total reaction mass; or
- the at least one catalyst is the sulfuric acid, and is present between 0.3-0.4 wt %, relative to the total reaction mass.

15. The process according to claim 8, wherein the activated (meth)acrylic acid derivate (III) is present in an amount of between 1.2 eq. and 1.6 eq., based on the amount of the alcohol of the general formula (II).

16. The process according to claim 9, wherein the reaction of the alcohol of the general formula (II) with the activated (meth)acrylic acid derivate (III) is carried out at a temperature between 85° C. and 95° C.

* * * * *